United States Patent
Bernal et al.

(10) Patent No.: US 10,201,293 B2
(45) Date of Patent: Feb. 12, 2019

(54) NON-CONTACT MONITORING OF SPATIO-TEMPORAL RESPIRATORY MECHANICS VIA DEPTH SENSING

(71) Applicant: Xerox Corporation, Norwalk, CT (US)

(72) Inventors: Edgar A. Bernal, Webster, NY (US); Eribaweimon Shilla, Karnataka (IN); Himanshu Madhu, Webster, NY (US); Lalit K. Mestha, Fairport, NY (US); Robert P Loce, Webster, NY (US)

(73) Assignee: XEROX CORPORATION, Norwalk, CT (US)

( * ) Notice: Subject to any disclaimer, the term of this patent is extended or adjusted under 35 U.S.C. 154(b) by 755 days.

(21) Appl. No.: 14/223,402

(22) Filed: Mar. 24, 2014

(65) Prior Publication Data

US 2015/0265187 A1 Sep. 24, 2015

(51) Int. Cl.
*A61B 5/00* (2006.01)
*A61B 5/11* (2006.01)
*A61B 5/113* (2006.01)

(52) U.S. Cl.
CPC ............ *A61B 5/1128* (2013.01); *A61B 5/113* (2013.01); *A61B 5/4836* (2013.01); *A61B 5/7485* (2013.01); *A61B 5/7246* (2013.01); *A61B 2576/00* (2013.01)

(58) Field of Classification Search
None
See application file for complete search history.

(56) References Cited

U.S. PATENT DOCUMENTS

| | | | |
|---|---|---|---|
| 2006/0279428 A1* | 12/2006 | Sato | A61B 5/0064 340/575 |
| 2012/0289850 A1 | 11/2012 | Xu et al. | |
| 2013/0053718 A1* | 2/2013 | Hung | A61B 5/486 600/534 |
| 2013/0324830 A1 | 12/2013 | Bernal et al. | |
| 2013/0324874 A1 | 12/2013 | Bernal et al. | |
| 2013/0324875 A1 | 12/2013 | Mestha et al. | |
| 2013/0324876 A1 | 12/2013 | Bernal et al. | |
| 2013/0342756 A1 | 12/2013 | Xu et al. | |
| 2013/0343634 A1 | 12/2013 | Xu et al. | |
| 2014/0142729 A1* | 5/2014 | Lobb | G06F 3/011 700/90 |

OTHER PUBLICATIONS

U.S. Appl. No. 14/023,654, filed Sep. 11, 2013, Mestha et al.

(Continued)

*Primary Examiner* — Thomas Hong
*Assistant Examiner* — Marjan Saboktakin
(74) *Attorney, Agent, or Firm* — Fay Sharpe LLP

(57) ABSTRACT

Systems and methods are proposed for non-contact monitoring of spatio-temporal mechanics comprising motion patterns of respiratory muscles, lungs and diaphragm. The depth capable sensors system is comprised of modules, including a depth estimation module, a reference shape generation module, a region of interest shape estimation module, and a shape comparison module. A recommender module is optionally included. The acquisition of spatio-temporal respiratory mechanic data comprising a time varying sequence of spatially dependent representations of the respiratory mechanics of the subject are processed for identifying differences between the subject's actual respiratory mechanics and desired mechanics that can improve the health of the subject, or identify particular maladies.

10 Claims, 12 Drawing Sheets

(56) References Cited

OTHER PUBLICATIONS

U.S. Appl. No. 14/044,043, filed Oct. 2, 2013, Mestha et al.
U.S. Appl. No. 13/680,838, filed Nov. 19, 2012, Bernal et al.
American Lung Association, Epidemiology and Statistics Unit Research and Program Services Division, Research and Health Education Division: "Trends in Asthma Morbidity and Mortality", American Lung Association. Washington, DC: American Lung Association; 2012.
Zahran, HS, Bailey C, Garbe P., "Vital Signs: Asthma Prevalence, Disease Characteristics, and Self-Management Education—United States, 2001-2009", MMWR Morb Mortal Wkly Rep 2011; 60(17); 547-552, http://www.cdc.gov/mmwr/preview/mmwrhtml/mm6017a4.htm, 12 pages.
Akinbami, LJ, Moorman, JE, Liu, X. Asthma Prevalence, Health Care Use, and Mortality: United States, 2005-2009. National Health Statistics Report. 32. Hyattsville, MD: National Center for Health Statistics; 2011. PMID: 21355352. 15 pages.
Product information—QVAR®. 2008. www.accessdata.fda.gov/drugsatfda_docs/label/2008/020911s017lbl.pdf. 2008.
Highlights of Prescribing Information—Proair HFA. 2010 www.accessdata.fda.gov/drugsatfda_docs/label/2010/021457s021lbl.pdf.
Partridge, M. R., Dockrell M., Smith N.M.: "The Use of Complementary Medicines by Those with Asthma", Respir Med Apr. 2003; 97(4):436-438. PMID: 12693806.
Shaw, Alison, Thompson, Elizabeth A., Sharp, Debbie: "Complementary therapy Use by Patients and Parents of Children with Asthma and the Implications for NHS Care: A Qualitative Study", BMC Health Services Research 2006; 6:76. PMID: 16776833, 12 pages.
"COPD (Chronic Obstructive Pulmonary Disease" Nhlbi.nih.gov Feb. 15, 2012 http://www.nhlbi.nih.gov/health/public/lung/copd/, 2 pages.
"2007 NHLBI Morbidity and Mortality Chart Book" (pdf), 113 pages. http://www.nhlbi.nih.gov/resources/docs/07a-chtbk.pdf.
Breathing Exercises Treat COPD, http://www.realnatural.org/breathing-exercises-treat-copd © Copyright 2014, 3 pages.
Tangelder, J., Veltkamp, R.: "A Survey of Content Based 3D Shape Retrieval Methods", Multimedia Tools Application vol. 39: 2008.

\* cited by examiner

NON-CONTACT MONITORING OF SPATIO-TEMPORAL RESPIRATORY MECHANICS VIA DEPTH SENSING

CROSS REFERENCE TO RELATED PATENTS AND APPLICATIONS

"Processing a Video for Tidal Chest Volume Estimation," E. Bernal, L K Mestha, B. Xu, U.S. Patent Publication No. US 2013-0324876 A1, published Dec. 5, 2013.

"Generating A Flow-Volume Loop For Respiratory Function Assessment", L K Mestha, E. Shilla, E. Bernal, H. Madhu, U.S. patent application Ser. No. 14/023,654, filed Sep. 11, 2013.

"Breathing Pattern Identification For Respiratory Function Assessment", L K Mestha, E. Shilla, E. Bernal, H. Madhu, G. Pennington, U.S. patent application Ser. No. 14/044,043, filed Oct. 2, 2013.

INCORPORATED REFERENCES

The following U.S. Patents, U.S. Patent Applications, and Publications are incorporated herein in their entirety by reference.

"Processing A Video For Tidal Chest Volume Estimation", U.S. Patent Publication No. US 2013-0324876 A1, published Dec. 5, 2013, by Bernal et al. which discloses a system and method for estimating tidal chest volume by analyzing distortions in reflections of structured illumination patterns captured in a video of a thoracic region of a subject of interest.

"Minute Ventilation Estimation Based On Depth Maps", U.S. Patent Publication No. US 2013-0324830 A1, published Dec. 5, 2013, by Bernal et al. which discloses a system and method for estimating minute ventilation based on depth maps.

"Minute Ventilation Estimation Based On Chest Volume", U.S. Patent Publication No. US 2013-0324874 A1, published Dec. 5, 2013 by Bernal et al. which discloses a system and method for estimating minute ventilation based on chest volume by analyzing distortions in reflections of structured illumination patterns captured in a video of a thoracic region of a subject of interest.

"Processing A Video for Respiration Rate Estimation", U.S. Patent Publication No. US 2013-0324875 A1, published Dec. 13, 2013, by Bernal et al. which discloses a system and method for estimating a respiration rate for a subject of interest captured in a video containing a view of that subject's thoracic region.

"Respiratory Function Estimation From A 2D Monocular Video", U.S. patent Ser. No. 13/680,838, filed Nov. 19, 2012, by Bernal et al. which discloses a system and method for processing a video acquired using an inexpensive 2D monocular video acquisition system to assess respiratory function of a subject of interest.

"Monitoring Respiration with a Thermal Imaging System", U.S. Patent Publication No. US 2012-0289850 A1, published Nov. 15, 2012, by Xu et al. which discloses a thermal imaging system and method for capturing a video sequence of a subject of interest, and processing the captured images such that the subject's respiratory function can be monitored.

"Enabling Hybrid Video Capture Of A Scene Illuminated With Unstructured And Structured Illumination Sources", U.S. Patent Publication No. US 2013-0342756 A1, published Dec. 26, 2013, by Xu et al. which discloses a system and method for enabling the capture of video of a scene illuminated with unstructured and structured illumination sources.

"Contemporaneously Reconstructing Images Captured Of A Scene Illuminated With Unstructured And Structured Illumination Sources", U.S. Patent Publication No. US 2013-0343634 A1, published Dec. 26, 2013, by Xu et al. which discloses a system and method for reconstructing images captured of a scene being illuminated with unstructured and structured illumination sources.

TECHNICAL FIELD

The present invention is directed to systems and methods for identifying a patient's breathing pattern and mechanics for respiratory function assessment.

BACKGROUND

The respiratory system, which is responsible for ventilation, is one of the most essential vital systems in the human body. Consider the healthcare impact of a few respiration maladies. In 2009, an estimated 8.2% of Americans (9.6% of children and 7.7% of adults) had asthma, and the prevalence of asthma has increased substantially in recent years. In 2007, asthma accounted for 456,000 hospitalizations and more than 3,447 deaths. Persistent asthma treatment includes the use of long-term control medications (most commonly inhaled corticosteroids [ICS]) to reduce airway inflammation and quick-relief medications for acute exacerbations. While the benefits of asthma treatment generally outweigh the potential risks, these medications can be associated with adverse effects. Additionally, some asthma patients have concerns about asthma medications, and some patients would likely prefer to reduce their use of medication if alternative treatments were available. Twenty-seven percent of children with asthma report using complementary and alternative medicine to manage their asthma, and this approach was usually a breathing technique of some kind. Worldwide, chronic obstructive pulmonary disease ("COPD") ranked as the sixth leading cause of death in 1990. Mortality is expected to increase due to an increase in smoking rates and an aging population in many countries. COPD is the third leading cause of death in the U.S., and the economic burden of COPD in the U.S. in 2007 was $42.6 billion in health care costs and lost productivity. Many researchers have found that nurse-led breathing exercises in the home are significantly more effective for COPD patients with stage 3 or 4 COPD compared with standard medical care for COPD. The ability to monitor the mechanics of respiration has the potential to have a significant impact on respiratory healthcare treatments and the cost of healthcare. Respiratory diseases usually manifest themselves in abnormal spatio-temporal breathing patterns such as those involving excessive chest or shoulder movement. In addition, monitoring thoracoabdominal or abdominothoracic motion breathing patterns is useful to assess the respiratory health of an individual.

The goal of respiration is to provide gas exchange: to supply oxygen to and remove carbon dioxide from tissues. Pulmonary ventilation refers to the movement of air in and out between the atmosphere and the alveoli. The mechanics of ventilation are mainly driven by the muscles which cause lung expansion and contraction. Spirometry equipment traditionally employed to perform such monitoring usually relies on the patient wearing belts or breathing into tubes.

While some aspects of the mechanics of respiration can be captured by single parameters such as the aforementioned respiration rate, volumes, flows and pressures, all of which can be measured with current spirometry equipment, certain parameters that relate to the motion mechanics localized to certain regions of the respiratory process (e.g., of the respiratory muscles, the diaphragm and the thoracic cavity) are difficult to quantify with existing technology during inspiratory and expiratory maneuvers of various kinds. For example, airflow resistance and compliance may be different for the left bronchial tree when compared to the same present on the right side. This uneven property will manifest as a difference in spatio-temporal signals on the chest surface between the left and right sides of the thoracic cage. Lung volume may be different on one side due to differences in transpulmonary pressures (the pressure difference in the alveoli in the lungs and the intrapleural pressure) from one side to the other. These differences may be the result of infections or various respiratory related disease conditions. As noted above, existing spirometry technologies are unable to monitor such a plurality of parameters because at any given instant in time, they only measure a single parameter of interest (e.g., respiratory volume, respiratory flow, breathing frequency, respiratory flow rate, etc.) and do not provide spatially dependent parameters.

There is a need for improved non-contact methods and systems to quantify and monitor aspects of the spatio-temporal respiration mechanics that remain unaddressed by existing spirometry equipment.

There is a need for identifying and analyzing the multi-dimensional spatio-temporal respiration mechanics for determining problems therewith and to suggest improved mechanics for better subject health. More particularly, there is a need for the monitoring of certain parameters of the respiration mechanics, such as the motion patterns of the respiratory muscles and organs (lungs and diaphragm) involved in the respiratory process.

BRIEF DESCRIPTION

According to aspects illustrated herein, there is provided methods and systems for generating a representation of spatio-temporal respiratory mechanics of a subject via non-contact depth sensing. The method comprises determining a sequential set of spatially dependent values representative of the respiratory mechanics of a patient. The values may comprise a depth map measurement of a region of interest of the subject. The shapes of the region of interests are estimated in a multi-dimensional model. The estimated shape can be compared with a reference shape or between selected areas of the region of interest for identifying differences therebetween. The representations are processed for identifying respiratory mechanics corresponding to a health problem of the subject. Thereafter, improved respiratory mechanics can be suggested to the subject for achieving better health.

The subject methods and systems utilize full range spatial depth sensing capabilities provided by non-contact spirometry.

DETAILED DESCRIPTION

Figure 1:
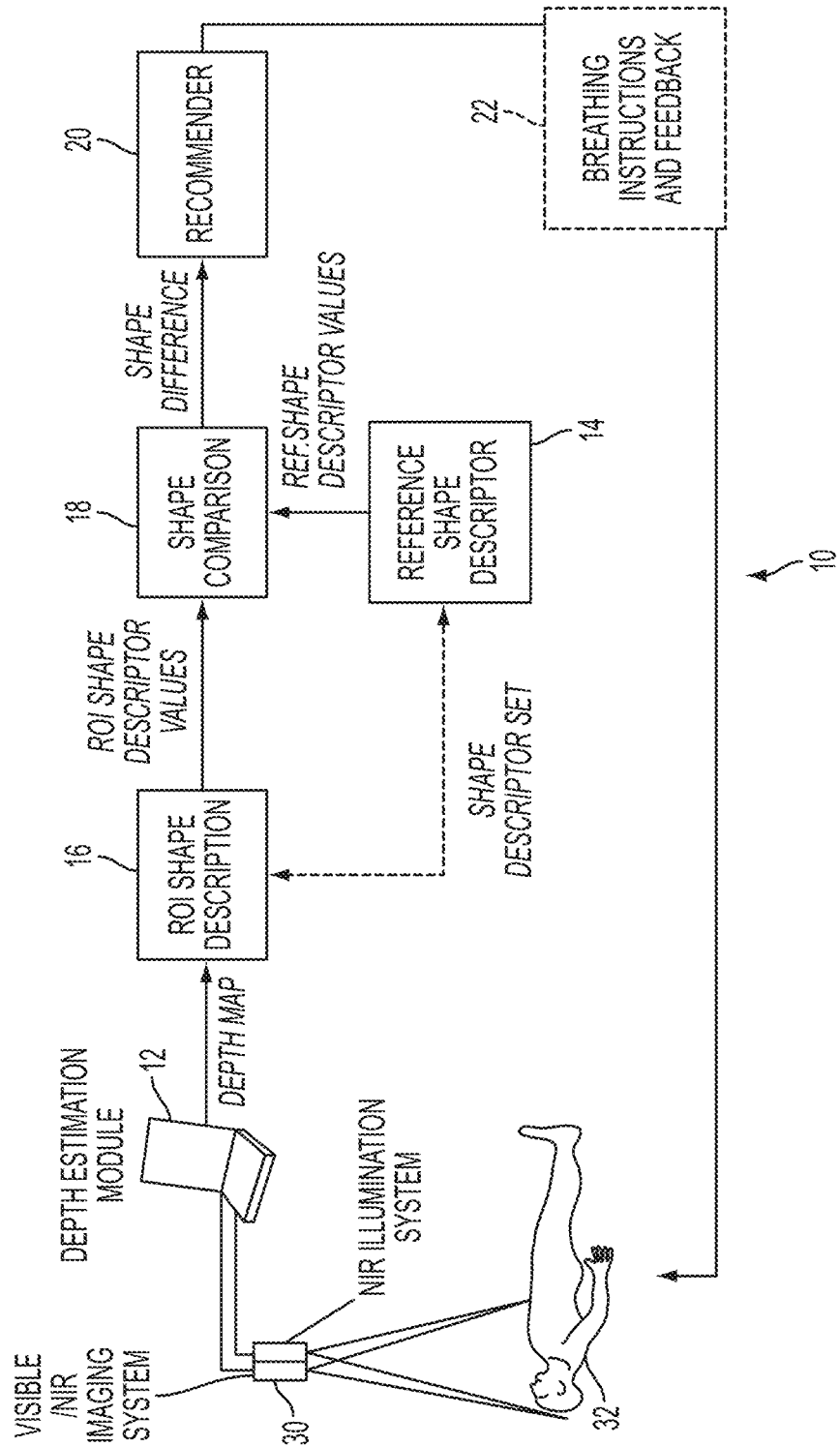
FIG. 1 is a block diagram of a high level overview of the modular componentry of the subject system.

The present embodiments are methods and systems for non-contact monitoring of spatial-temporal respiratory mechanics via depth sensing. More particularly, the embodiments comprise a monitoring of certain parameters of the respiration mechanics such as the motion patterns of the inspiratory and expiratory muscles and organs (rib cage, lungs, diaphragm) involved in the respiratory process.

The following phrases and terms will be used throughout the detailed description and so intended meanings are provided, but the terms are not limited to any precise definitions. It should be appreciated that various other features and functions, or alternatives thereof, may be subsequently construed by those skilled in the art which are also intended to be encompassed by these explanations.

NON-LIMITING DEFINITIONS

A "subject of interest" refers to a person or patient being monitored for respiratory function assessment. It should be appreciated that the use of the terms "human", "person", or "patient" herein is not to be viewed as limiting the scope of the appended claims solely to human subjects.

A "target region or region of interest ("ROI")" refers to an area or region of the subject where respiratory function can be assessed. For example, the target region may be a subject's anterior thoracic region, abdominal region, a region of the subject's dorsal body, and/or a side view containing the subject's thoracic region. Note that the thoracic region includes the shoulder region. It should be appreciated that a target region can be any view of a region of the subject's body which can facilitate respiratory function assessment. The abdominal area is also especially of interest as it is critical to breathing dynamics.

"Respiration" is a process of inhaling of air into lungs and exhaling air out of the lungs involving gas exchange to the cells (i.e., oxygen to the cell and carbon dioxide to the outside air). Inhalation is an active process caused by a negative pressure having been induced in the chest cavity by the contraction of a relatively large muscle (often called the diaphragm) which changes pressure in the lungs by a forcible expansion of the lung's region where gas exchange takes place (i.e., alveolar cells). Exhalation is a passive process where air is expelled from the lungs by the natural elastic recoil of the stretched alveolar cells and connective tissue, as well as by muscular relaxation. The lining of alveolar cells has a surface-active phospholipoprotein complex which causes the lining of the lungs to naturally contract back to a neutral state once the external force causing the cell to stretch is released. A post-expiratory pause occurs when there is an equalization of pressure between the lungs and the atmosphere.

"Depth map" is a reconstructed surface map or temporal sequence thereof describing the distance between a target region of a subject and a depth sensing system. There is a plurality of techniques known in the art for obtaining a depth map of a target region. In one embodiment, where an active stereo sensing system is used, a depth map is reconstructed by projecting a pattern of light with known spatial attributes, establishing correspondences between spatial attributes in a detected pattern and spatial attributes of the projected undistorted pattern, and triangulating the established correspondences to characterize offsets or displacements therebetween. Correspondences are established with the aid of coding techniques. These offsets are converted to absolute depth values based on the known relative placement between the imaging device and the projector, as well as on the intrinsic parameters of the projector and imaging device in a process known as triangulation. When the relative placement or the parameters are not known, relative depth values can still be obtained via triangulation. In another embodiment where a passive stereo sensing system is used, a depth map is generated by characterizing offsets or displacements between locations of salient features identified in the images captured by at least two imaging devices with overlapping fields of view of the scene. These offsets are converted to absolute depth values which comprise the depth map using a conversion which is based on the offsets, the known relative placement between the at least two imaging devices, and the intrinsic parameters of the imaging devices. The depth map can also comprise relative values which are obtained when some of the parameters in the system are not known. Depth values of locations not associated with the salient features can be interpolated from the depth values of locations associated with the salient features. In yet another embodiment where a time-of-flight system is used, a depth map is then reconstructed by aggregating a plurality of point depth measurements corresponding to a plurality of points in the scene, each of the plurality of depth measurements obtained by point-by-point range measurement. A multiplicity of depth measurements can be acquired by sweeping the point-by-point device or by arranging them in one- or two-dimensional arrays. In yet another embodiment, a depth map may be constructed based on the amount of deformation in a known pattern comprising, for instance, textural characteristics present on the target region itself such as skin blemishes, scars, markings, and the like, which are detectable by a traditional monocular video camera's detector array.

"Receiving depth maps" is intended to be widely construed and includes to download, upload, estimate, measure, obtain, or otherwise retrieve from a memory, hard drive, CDROM, or DVD or other non-transitory storage medium for storing and processing instructions readable and executable by an electronic data processing device. The depth maps are measured with a depth-capable sensing device. It should be appreciated that depth maps can be obtained using a camera to capture images of the subject while illuminated by a projected pattern of structured light, the camera being sensitive to a wavelength range of the structured light. The depth maps are then generated based upon a comparison of spatial characteristics of reflections introduced by a movement in the subject's chest cage to known spatial characteristics of the projected patterns in conjunction with the known distance between the light projector and the camera, and using the characterized distortions at different locations to calculate the depth map for each image in the video. Depth maps can be generated using distortions in patterned clothing worn by the subject.

A "reference ROI" refers to a representation that is associated with a known pattern of breathing. By a comparison of one or more segments of the subject's breathing signal against reference breathing signals which are associated with known breathing patterns, a pattern can be identified for the subject's breathing. The reference breathing signal can be retrieved from, for example, a memory, a storage device such as a hard drive or removable media, or received from a remote device over a wired or wireless network. The reference breathing signal may be images or representative signals generated using the depth capable sensor in a simulated environment by a respiratory expert. It can also be generated using the depth capable sensor on patients with identified respiratory diseases. For example, the reference breathing signal may be obtained on the subject at a reference time (e.g., before the subject is released from a hospital, at the onset of a therapy program, etc.) which may be compared to a later breathing signal in order to track the respiratory health of the subject over time.

A "subject's respiratory mechanics" refers to a temporal sequence of spatial measurements across time intervals during a period of inhalation and exhalation breathing. The measurements are obtained from processing the depth maps. In one embodiment, the depth map comprises a 3D hull defined by a set of 3D coordinates in space, namely their horizontal, vertical and depth coordinates (x, y and z respectively). Points in the hull can be used to form a triangular tessellation of the target area. By definition of a tessellation, the triangles fill the whole surface and do not overlap. The coordinates of an anchor point at a given depth are computed. The anchor point can be located on a reference surface, for example, the surface on which the subject lies. The anchor point in conjunction with the depth map defines a 3D hull which has a volume. Alternatively, the coordinates of points on an anchor surface corresponding to the set of depths of a reference surface can be computed. The anchor surface in conjunction with the depth map also defines a 3D hull which has a volume. A volume can be computed for each 3D hull obtained from each depth map. A concatenation of all sequential measurements forms a temporal sequence of representations of respiratory mechanics across time intervals during inspiration and expiration.

"3D shape descriptors and similarity metrics" usually focus on attributes like surface characteristics, as opposed to attributes such as color and texture, which are better suited for 2D image description. 3D shape descriptors can be broadly classified into feature- and graph-based. A 3D shape can be described by a set of points in the 3D space, each point having a specific three-dimensional coordinate. Describing a shape can be achieved by constructing a numeric representation of the mesh formed by the set of points; said representation is usually denoted a signature or descriptor. Measuring 3D shape similarity is an important task in shape retrieval and clustering. Computation of similarity metrics descriptors is tightly related to the 3D descriptor of choice, as similarity/dissimilarity metrics are usually computed in the descriptor space and are always relative to it. The use of local curvature descriptors are proposed to characterize the shape of various surfaces involved in the respiratory process, as well as to measure distances between an intended or ideal configuration and a measured shape. It should be noted, however, that other shape descriptors such as texture descriptors can be used interchangeably. When graph-based descriptors are used, similarities between two surfaces are measured by performing non-rigid surface matching, which essentially registers the two surfaces. Once the surfaces are registered, differences between the 3D coordinates of the registered surfaces can be used as indicators of surface dissimilarities. Alternatively, combinations of graph- and feature-based techniques can be used, for example by first performing surface matching, then extracting features of the registered surfaces and measuring similarity in the feature domain.

In some cases, similarities between temporal sequences of 3D shapes are measured. In these cases, in addition to spatial registration, temporal registration takes place between a reference and a measured or estimated 4D signal comprising sequences of 3D measurements. In one embodiment, the 4D signals are reduced to 2D signals by mapping each instantaneous 3D measurement to a 1D measurement, for example, to obtain two volumetric temporal sequences, one measured and one reference sequence. Traditional temporal registration techniques of temporal sequences of data can be implemented between the resulting volumetric temporal sequences. Once temporal registration is achieved, shape registration across the synchronized temporal scales can be performed. In another embodiment, registration of the 4D sequences is performed in the 4D space, for example, by estimating a 4D deformable transformation model which registers the temporal and the spatial coordinates of the measured and reference signals simultaneously.

The subject embodiments comprise a system for non-contact monitoring of spatio-temporal respiratory mechanics via depth-capable imaging devices that is suited for monitoring the motion mechanics of the respiration process. A subject 32 is monitored by an imaging system 30 for identifying his respiratory motion mechanics. This monitoring can be of importance in tasks such as respiratory therapy, supervising breathing exercises and in patients who need monitoring to obtain longitudinal data.

With reference to FIG. 1, the system 10 comprises the following modules: (1) a depth map estimation module 12 that reconstructs a temporal sequence of depth-maps of the region of interest (usually a subject's thoracic cage and abdominal region); (2) a reference shape generation module 14 that generates depth maps associated with a desired target shape to be achieved by the region of interest (typically depending on the application); (3) a region of interest shape estimation module 16 which estimates the shape of the region of interest (ROI) in the form of measured depth maps or 3D models of the ROI; (4) a shape comparison module 18 which extracts shape descriptors from the depth maps produced by modules 14 and 16 and determines (and possibly displays) the more salient differences between the reference shape generated by the reference shape and the region of interest shape estimated by module 16; and, optionally a recommender module 20 that emits suggestions aimed at aiding the subject achieve a better match between the target shape output by module 16 and the measured shape output by module 14; alternatively, if the match is considered acceptable for the specific task, this module 20 can issue positive reinforcement feedback.

The particular details of the subject monitoring and imaging system are conventional in its ability to represent spatio-temporal data corresponding to the patient respiration mechanics in a manner to allow the system to properly identify the mechanics over a selected period of time. For example, a target ROI could be a subject's anterior thoracic region, a region of said subject's dorsal body, and/or a side view containing said subject's thoracic region. FIG. 1 shows one such system employing a near infrared (NIR) illumination system and an associated visible/NIR imaging system. Other types of radiant energy monitoring of the patient's respiratory mechanics could of course be used. For example, the sensing device 30 could be a red green blue depth (RGBD) camera, an infrared depth camera, a passive stereo camera, an array of cameras, an active stereo camera, and a monocular video camera, or from data captured using a non-image-based depth sensing device comprising any of: a LADAR device, a LiDAR device, and a time-of-flight measurement device.

The data acquired by the imaging system 30 is communicated to the depth estimation module 12 (shown as a conventional computer-type data processing device) for the reconstruction of the temporal sequence of depth-maps of the region of interest such as a subject's thoracic cage and abdominal region. The depth estimation module 12 processes the sensed data from the imaging system 30 which can include a variety of depth-capable sensing technologies, such as, but not limited to, active and passive stereo systems, light detection and ranging systems (LiDAR) and time of flight systems. In one embodiment, an active stereo system has a structured illumination module to project patterns of NIR light onto the ROI, and a camera sensitive in the NIR band to observe the projected patterns. The depth characteristics of the scene can be estimated by characterizing the physical deformation that the pattern undergoes as it is reflected back from the objects in the ROI scene, as captured by the camera.

Alternatively, passive stereo systems, on the other hand, rely on the use of at least two cameras with a known baseline. As images of the scene are simultaneously captured with the cameras, the correspondence between pixels observing the same areas is determined. Depth of the scene at pixels where correspondences are found is estimated from the displacement or disparity between the corresponding pixels and the known baseline. 3D models of the ROI scene can also be recovered from overlapping views from multiple cameras.

LiDAR systems estimate the depth-map of the scene of interest by illuminating the scene with a narrow line width laser and analyzing the characteristics of the reflected light. Time of flight systems estimate depth by correlating it with the time it takes light from a given source to travel to and from different points on the scene.

Whatever sensing technology is employed, the resulting data is a representation of the patient's respiratory mechanics by identifying the ROI shape changes during the inhalation and exhalation of the respiration process. It is merely a matter of selection of what precise detail can be used in the monitored sequence. The more detailed the spatially dependent representations of the respiratory mechanics of the subject that are acquired, the more precise the subsequent analysis will be. Whatever data is generated by module 12 is broadly identified as a depth-map data and is communicated to the ROI shape description module 16.

Figure 2A:
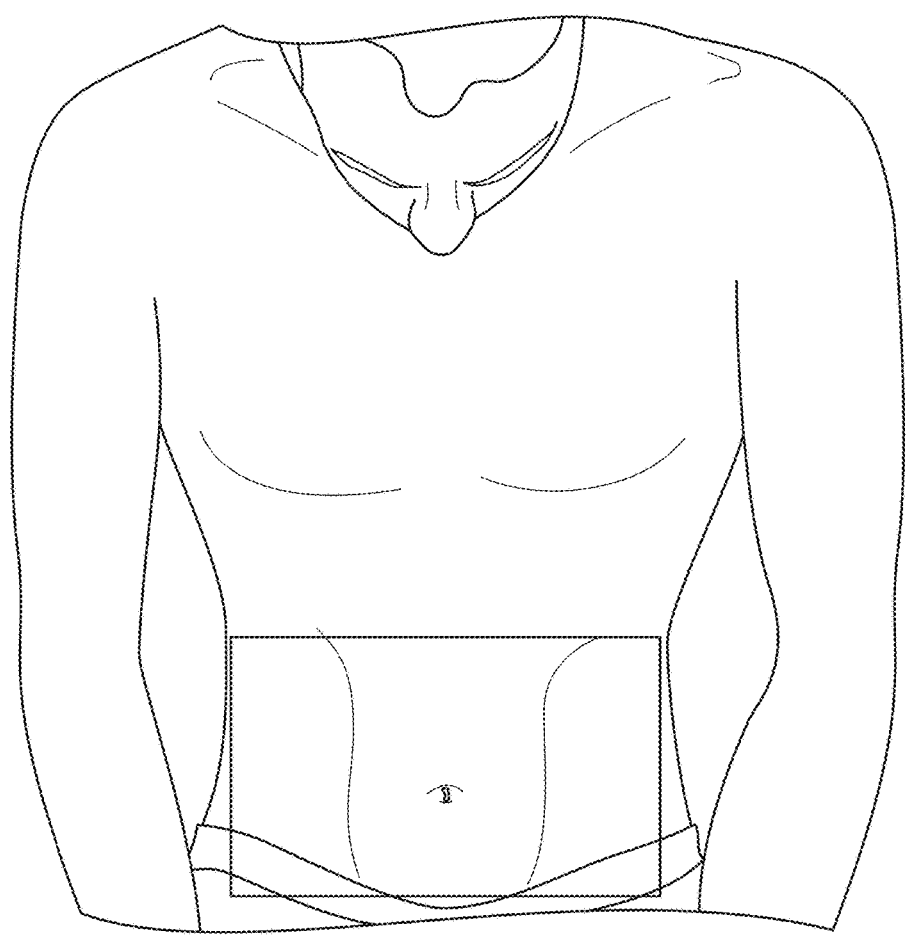
FIG. 2A shows a test subject and an associated region of interest.

The reference shape generation module 14 produces a reference shape description such as a sample depth map (or depth map sequences) of the ROI in an ideal or targeted configuration. In the context of breathing respiratory mechanics including exercises and therapies, a referenced shape depth map indicates the shape of the posture (or sequence of posture) that the subject needs to accomplish. FIG. 2a illustrates a rather extreme reference shape of inhalation executed by a Yoga instructor in a Nauli pose with the ROI, and FIG. 2b shows the corresponding synthetically generated reference depth map of the ROI.

Figure 2B:
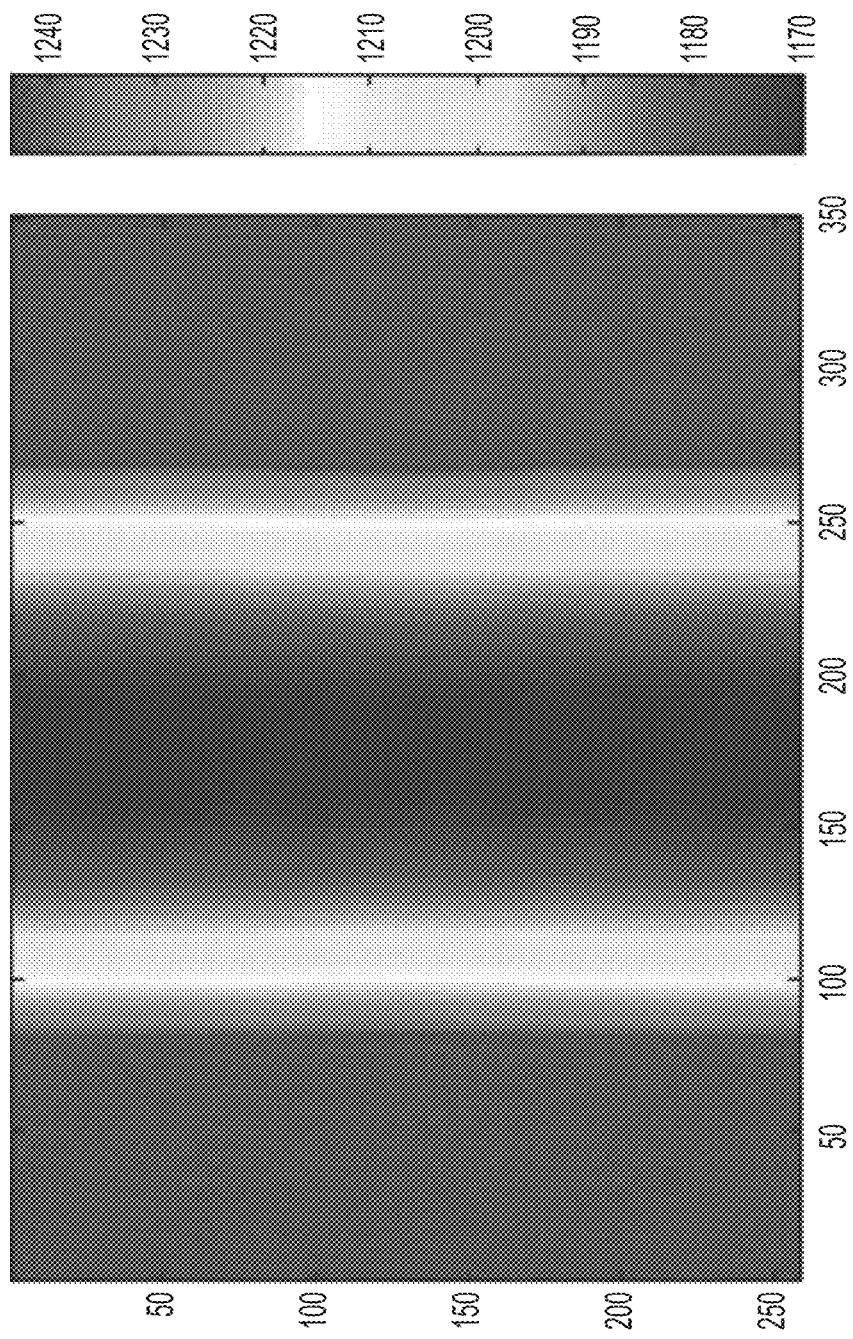
FIG. 2B shows the depth map for the ROI of FIG. 2A.

In this illustration the region of interest 36 is the abdominal area so that FIG. 2b illustrates the reference depth map of an abdominal region that satisfactorily complies with the reference posture of the target exercise. In other words, the depth map of FIG. 2b serves as a shape descriptor reference corresponding to the abdominal shape of the Yoga instructor's shape shown in FIG. 2a. Thus, the depth map of FIG. 2b can be output by the reference shape generation module 14 as a shape descriptor set of data for comparison with whatever depth map data is acquired by the depth estimation module 12 from the imaging of the subject 32. The target shape description in the form of a target depth map comprising a shape descriptor set needs to be measured directly from the region of interest of an expert practicing the exercise via the depth map estimation module 12, or it can also be produced synthetically, with input from therapists or instructors. The color axis in the figure indicates the relationship between the color of a pixel and its corresponding depth value, in millimeters. In FIG. 2b, the simulated depth map assumes that the sensor is about 1.2 m from the subject, which is a typical operational distance for a Kinect-based system. In one embodiment, the reference shape generation module 14 can also output shape descriptors associated with the reference shape. In the context of the present embodiments, the shape comparison module 18 extracts the necessary shape descriptors.

Figure 3A:
FIG. 3A shows a test subject and an associated region of interest.
Figure 3B:
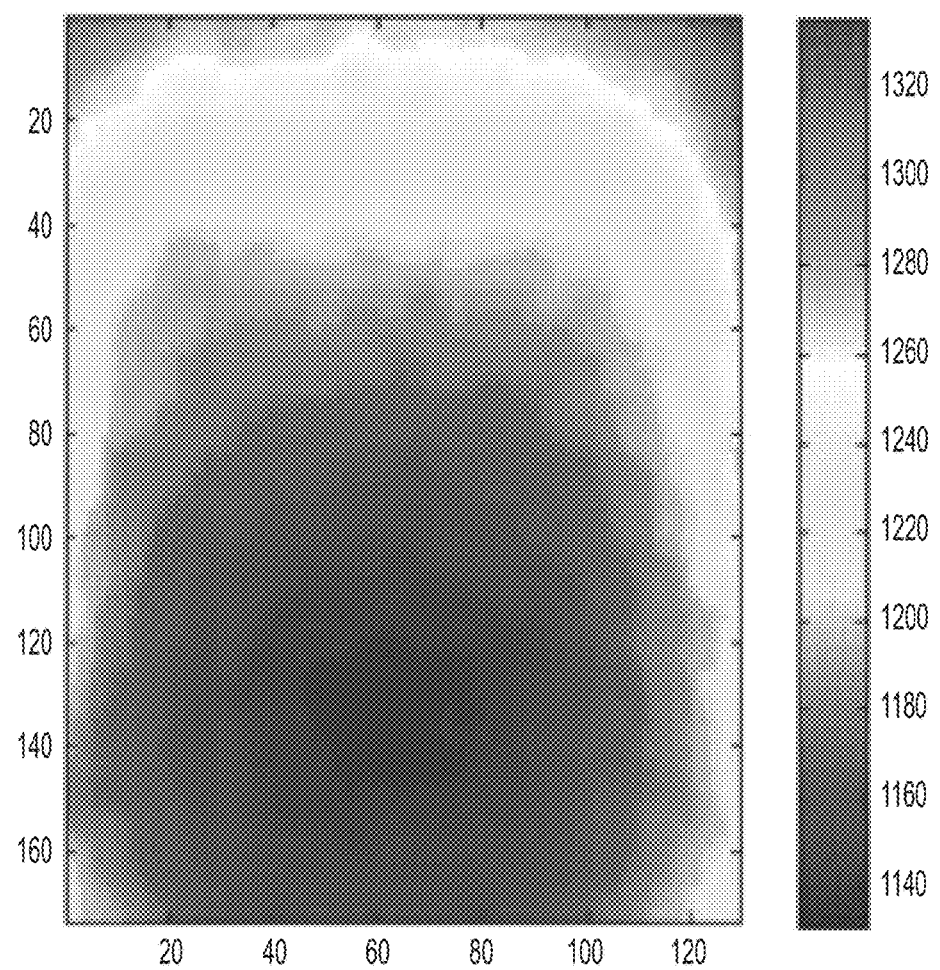
FIG. 3B shows the depth map for the ROI of FIG. 3A.

The region of interest shape estimation module 16 acquires the monitored data from depth map estimation module 12 and converts the data to ROI shape descriptor values that can be suitably compared to the reference shape descriptor values communicated from the reference shape generation module 14. The ROI shape estimation module 16 relies on the depth map estimation module 12 to estimate the shape of the region of interest in the form of measured depth maps or 3D models. FIG. 3a shows an image of a subject in a Yoga Ushtrasana pose, along with a manually located region of interest 40 comprising the thoracic cavity and the abdominal region. FIG. 3b shows the corresponding depth map (constructed with the proposed non-contact depth imaging system 30) in a color representation; the blue (red) end of the scale indicates shallow (deep) depth values and the measured depth is relative to the location of the depth sensor (deeper pixels are farther from the sensor). In one embodiment, the ROI shape estimation module can also output shape descriptors comparatively associable with the reference shape.

The shape comparison module 18 extracts shape descriptors from the depth maps produced by the reference shape generation module 14 and the ROI shape estimation module 16 and determines (and selectively displays) more salient differences between both shapes. A wide variety of 3D shape descriptors and their associated similarity/dissimilarity metrics are known that are aimed at shape matching or retrieval in general scenarios. Examples of descriptors include local (e.g., local curvature) and global (e.g., statistical moments of surface, volume-to-surface ratio, boundary descriptors) feature descriptors, graph-based methods, and geometry-based methods (e.g. view-based, volumetric, point-set descriptors).

In one present embodiment, a reduced range of possible shapes amounted to the configurations that the abdomen muscles and chest cavities can take on are employed. Since at any given moment, only a pair or few pairs of shapes need to be matched, the descriptors need not be extremely descriptive or discriminative. Suitable implementation would trade off computation complexity for the selected right amount of descriptiveness.

Figure 4A:
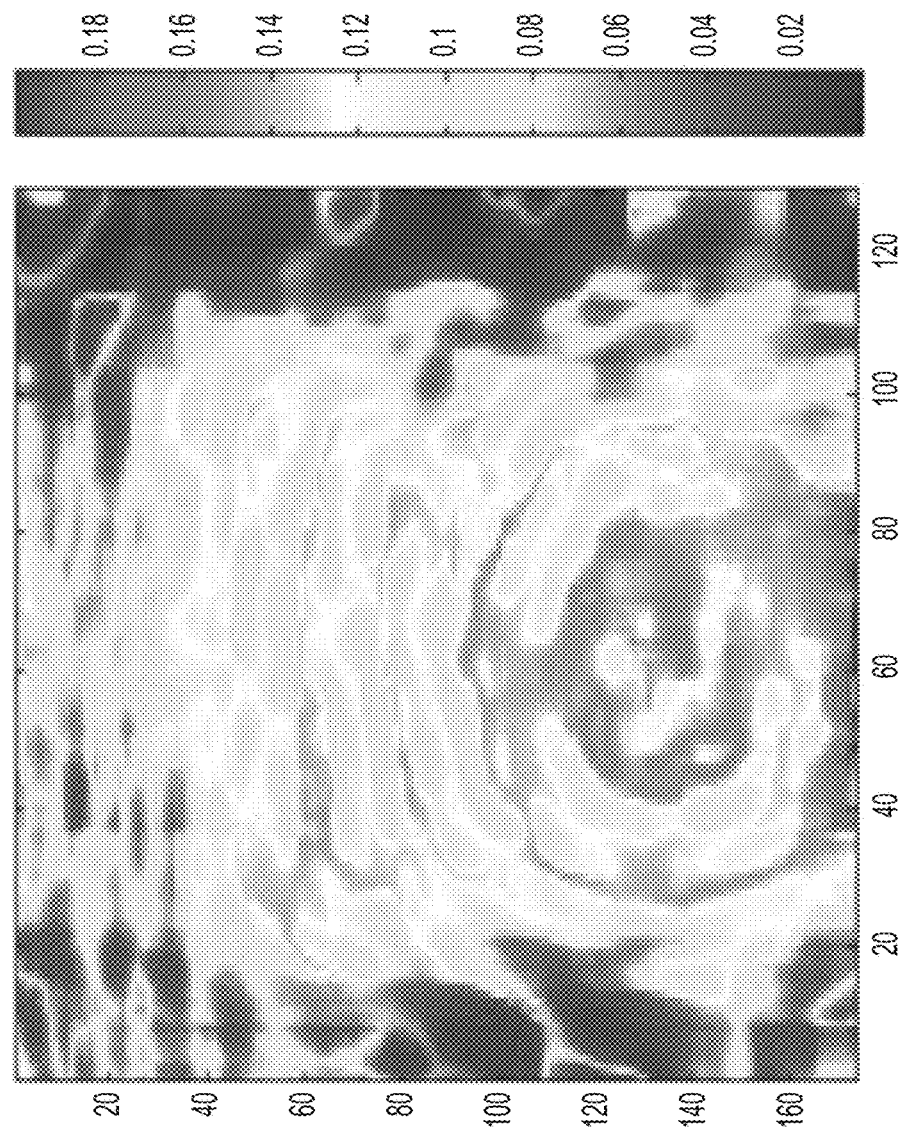
FIGS. 4A and 4B show sample sphere-based (circle-based) curvature maps computed from the depth maps in 2B and 3B, respectively.
Figure 4B:
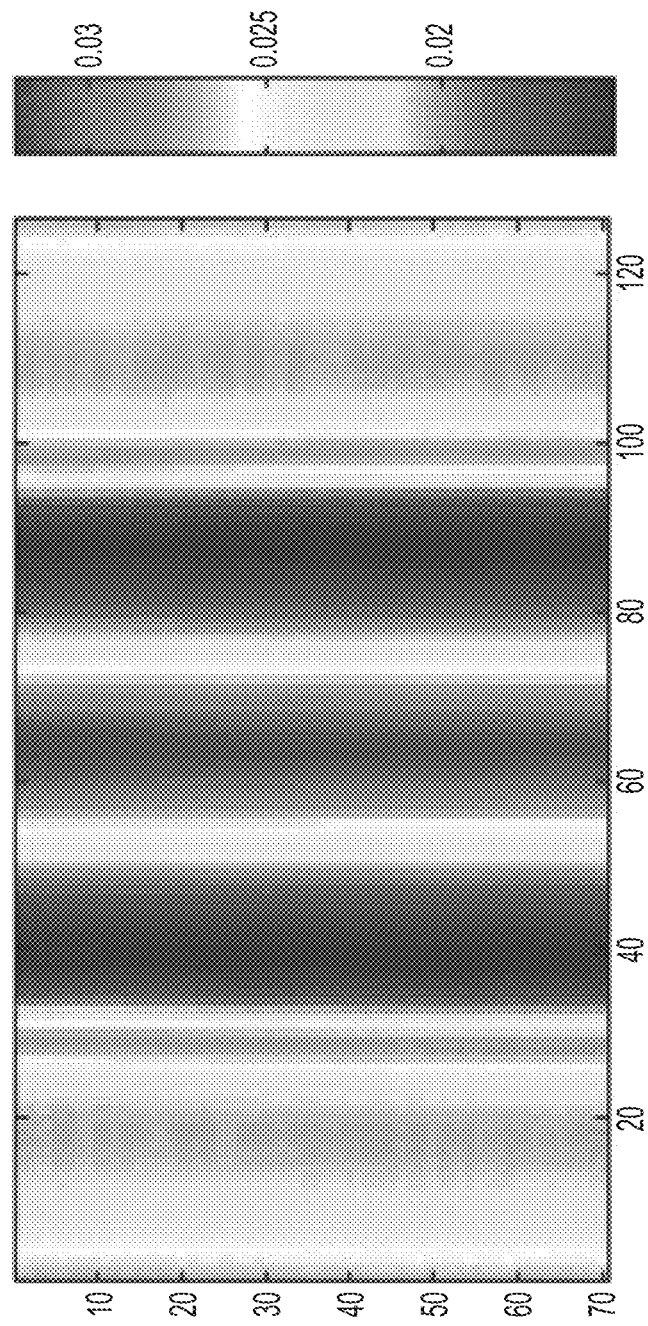

In one system implementation, a simple local curvature metric is used as a shape descriptor. Such a descriptor can work well on people with similar physiognomy; in order to match shapes on people with vastly different volume profiles, other features may be appropriate. Alternatively, different reference shape data sets for people with different body types can be built and used. The descriptors are computed on a pixel-by-pixel basis by fitting a circular or a sphere to a set of 3D cloud points within a row/column window or a two-dimensional window centered at the target pixel, respectively. The local curvature metric equals the inverse of the radius of the fitted sphere; smaller curvature numbers correspond to flatter regions and vice-versa. Positive curvature numbers correspond to convex surfaces, while negative curvature numbers correspond to concave surfaces. FIGS. 4a and 4b show sample sphere-based (circle-based) curvature map computed from the depth map in FIGS. 2b and 3b. Blank hues indicate regions of larger (smaller) local curvature. One-dimensional curvature metrics can be used for cases when the poses are symmetric with respect to some axis, which is often the case when dealing with abdominal shapes, where symmetry about the vertical axis is common. Other shape descriptors include those based on fitting to a primary shape, regression to a manifold model, or local gradient models.

Figure 5A:
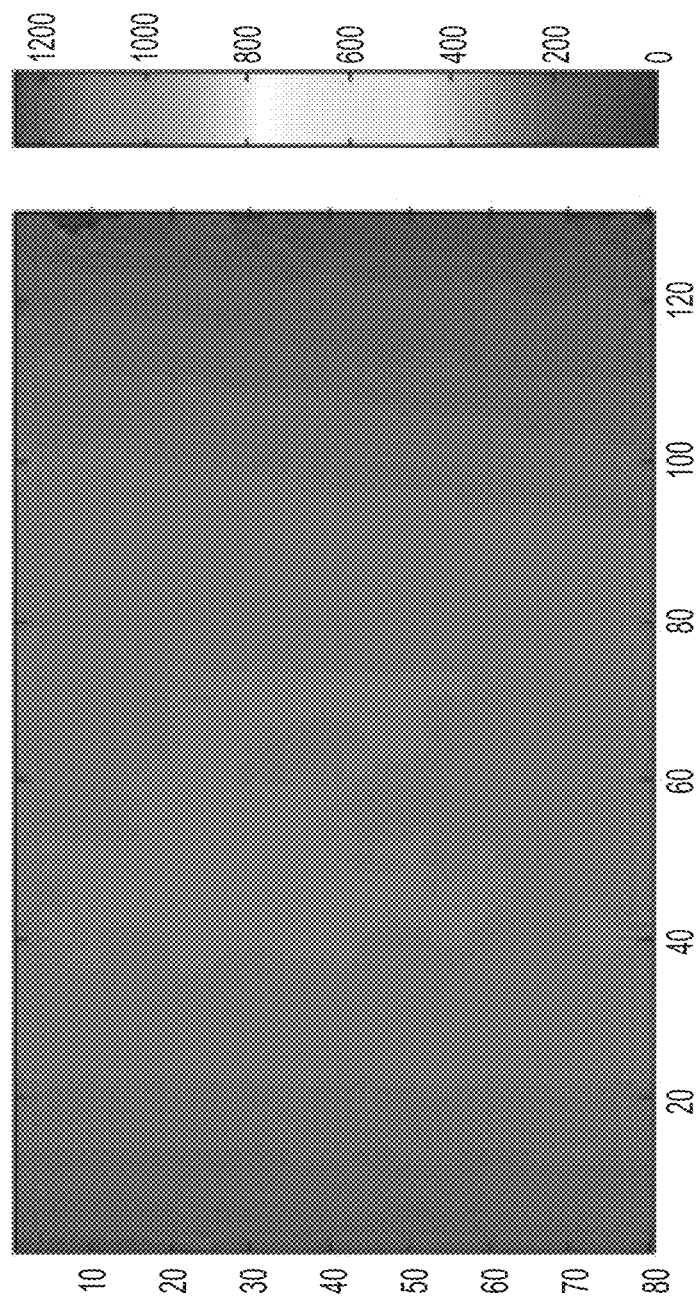
FIG. 5A is a depth map of the abdominal region of the subject in FIG. 2A.
Figure 5B:
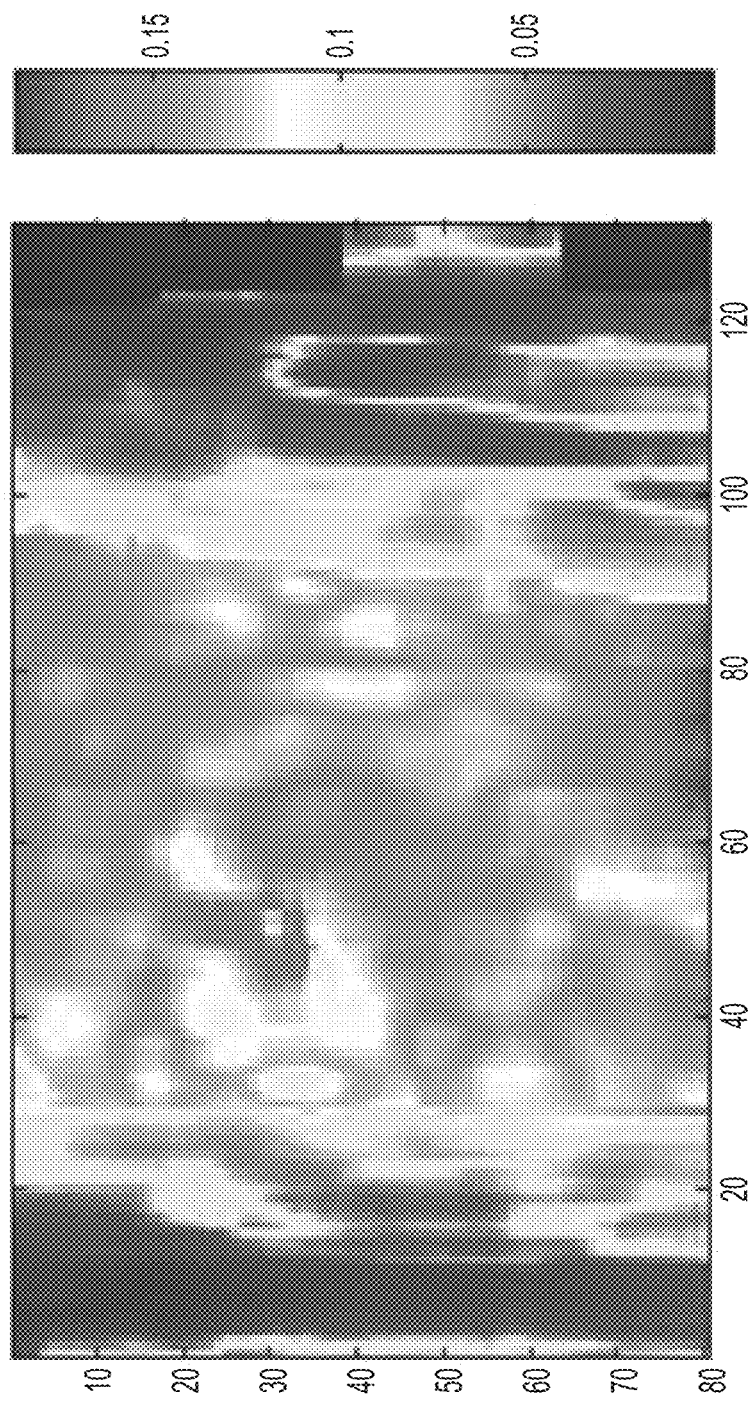
FIG. 5B is a local curvature map corresponding to FIG. 5A.
Figure 5C:
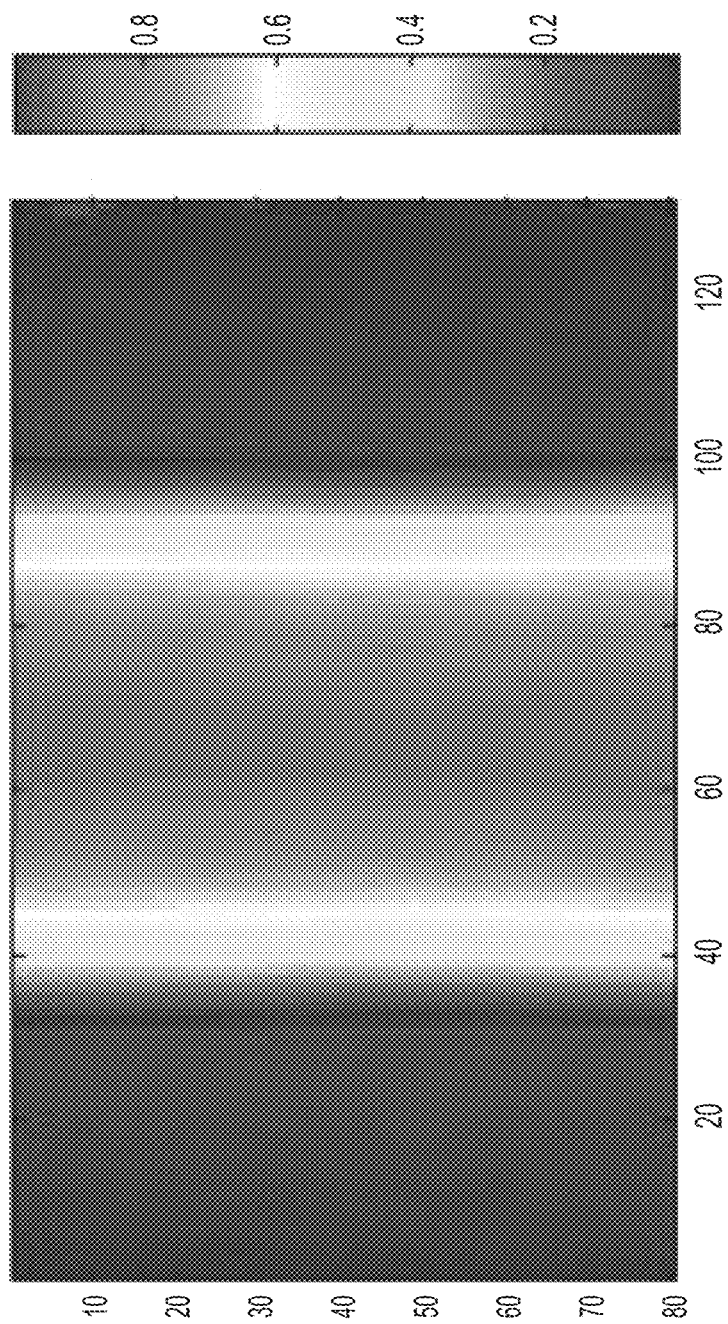
FIG. 5C is a representation of the differences between FIGS. 5A and 5B with regard to depth.
Figure 5D:
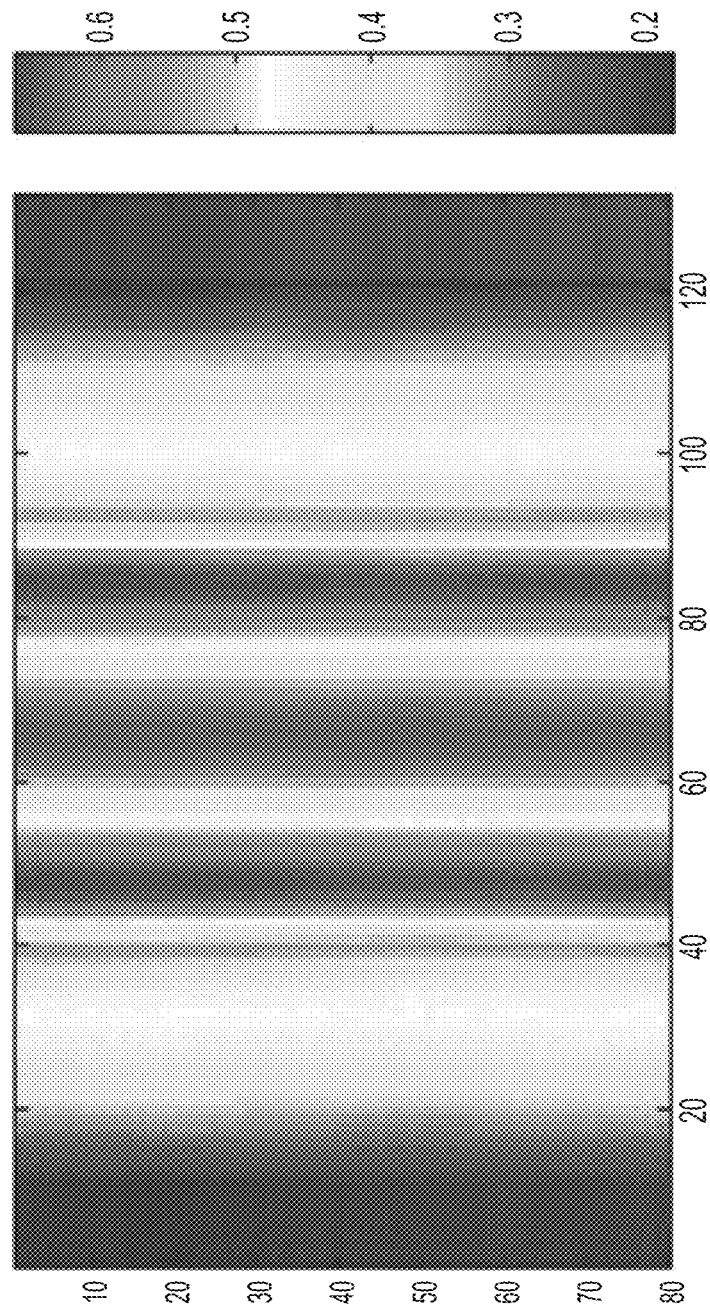
FIG. 5D is a representation of the differences between the measured maps of FIGS. 5A and 5B in the curvature domain.

Once shape descriptors from both the reference and the ROI maps have been extracted, the system proceeds to compute the differences between both representations, and, potentially, between the depth maps themselves as well. FIG. 5a corresponds to the abdominal region of a subject in preparation for the Nauli pose illustrated in FIG. 2a. Its corresponding curvature map is illustrated in FIG. 5b. FIGS. 5c and 5d illustrate (absolute) difference maps between the measured posture from FIG. 5a and the target posture from FIG. 2b in the depth and curvature domains, respectively. Inspection of FIGS. 5c and 5d indicate the largest sources of shape difference between the measured and the target shape. From these plots, a therapist or instructor can easily issue recommendations to the subject relative to which actions to perform in order to better match the target shape without the need for any contact measurement.

In an alternative embodiment, selected portions of the ROI shape descriptions can be segregated for respective comparison, instead of comparison with a third party reference shape. In other words, selected portions of a patient's determined shapes can be compared amongst themselves. For example, if the subject is suffering from a particular malady where one of his lungs contracts and expands at a smaller degree relative to the other lung, the identification of the malady does not need to resort to a third party reference shape. Proper identification can be accomplished by merely identifying that one side of the ROI shape is sort of different than the other side of the shape (i.e., one side has a bulge that the other lacks). In addition, the non-bulging side would seem to contract farther than the other side as determined in the time-varying sequence of shape representations acquired by the depth estimation module 12. Identification of relative differences in selected areas of the ROI is an alternative useful analysis, and avoids the need for having an absolute comparison with a target reference shape.

One exemplary reference practice is to obtain a reference shape on a subject at the time that the subject is released from care (e.g., upon leaving a hospital) to track the respiratory health of the subject over time since the care release.

Recommender module 20 emits suggestions aimed at aiding the subject achieve a better match between the target and measured shape; alternatively, if the match is considered acceptable for the specific task, this module can issue positive reinforcement feedback. Recommender module 20 is an option because the information from the shape comparison module 18 can be conveyed to an operator (e.g., a respiratory therapist, trained nurse, etc.) who would play the role of the recommender system either based on the output of the shape comparison module or by visual inspection of the reference and ROI shape estimation modules as illustrated above.

An automated recommender module 20 would analyze the difference maps output by the shape comparison module 18 and emit recommendations 22 to the user based on the characteristics of said maps, along with knowledge of the ROI location. Consistent with the examples above, given the locations of the regions with the largest depth and curvature differences, the module 20 would emit a recommendation 22 to engage the rectus abdominis and the oblique muscles, specifically by expanding the former and contracting the latter. This is indicated by the large depth differences along the rectus abdominis muscles as highlighted by FIG. 5c and the large curvature differences along the region bordering both muscles as indicated by FIG. 5d.

Figure 6:
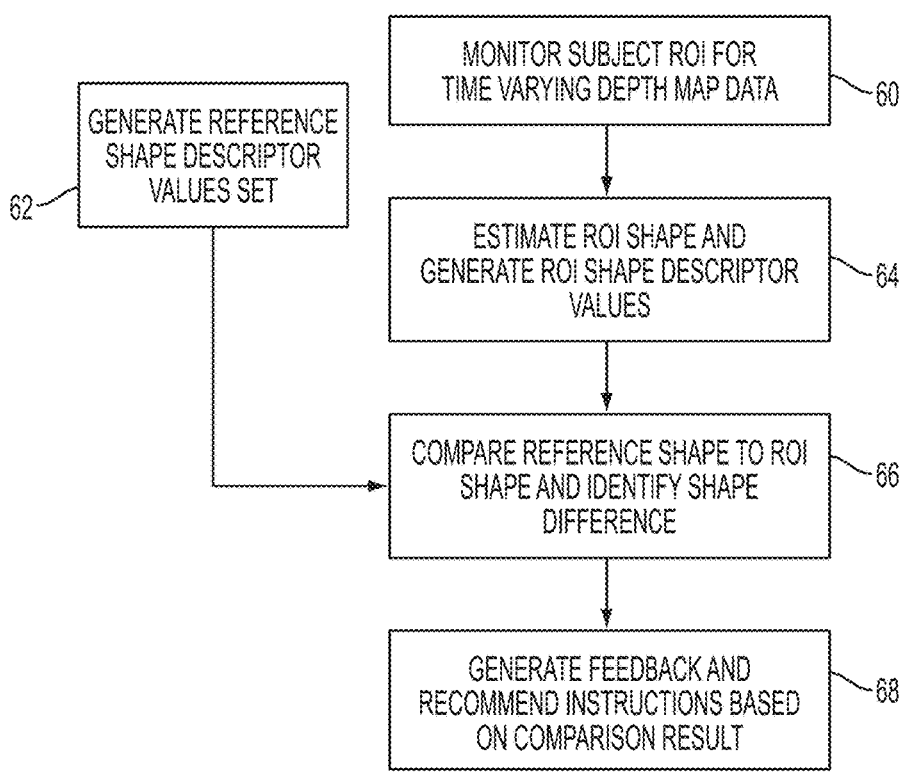
FIG. 6 is a flowchart of a method in accordance with the subject embodiments.

FIG. 6 illustrates the method steps practiced in the operation of the modules as described above. The depth estimation module 12 and the ROI shape estimation module 16 monitor 60 a subject's 32 ROI in the imaging system 30 for acquiring 64 the time-bearing depth map data and ROI shape descriptor values. A reference shape descriptor value set is generated 62 by the referenced shape generation module 14 in the form of a shape descriptor set comparable to the ROI shape descriptor values of the subject. As noted above, the referenced shape description may comprise a shape descriptor set from a third-party target shape, or may comprise a selected portion of the subject shape descriptor values such as in the example above of the comparing of the subjects left lung versus right lung respiratory mechanics. The referenced shape descriptor values are compared 66 to the ROI shape descriptor values for identifying a shape difference. The identified difference can be used to generate 68 feedback and instructions to improve the subject's respiratory mechanics.

The foregoing embodiments possess several advantages including the utilization of the full range of spatial depth sensing capabilities provided by the non-contact spirometry system 30 enabled by depth-capable sensors. The system objectively quantifies the motion mechanics of the respiratory process, which provides an advantage over more traditional qualitatively addressed diagnosis by a human (e.g., therapist, instructor, etc.). Volumetric spatio-temporal signals can allow the ability to examine the differences over time in airflow between left and right sides of the lungs. With high resolution depth-capable sensors the variations in muscle exertion and corresponding shapes can be regionalized for pinpointing which muscles exhibit weakness. Diseases often affect lung compliance, lung volume and airway resistance. Obstructive disorders are due to airway obstructions, often caused by narrowing of airways, sometimes spontaneously as in asthma. The subject type of spatial-temporal diagnosis without the invasive clinically cumbersome procedures of the prior art can improve patient care.

It will be appreciated that variants of the above-disclosed and other features and functions, or alternatives thereof, may be combined into many other systems or applications. Various presently unforeseen or unanticipated alternatives, modifications, variations or improvements therein may be subsequently made by those skilled in the art which are also intended to be encompassed by the following claims.

What is claimed is:

1. A system for generating a representation of spatio-temporal respiratory mechanics of a subject via non-contact depth sensing, comprising:
   a reference shape generation processor configured for generating reference shape descriptor values;
   a depth sensing device configured for determining a time-varying sequence of spatially dependent representations of the respiratory mechanics of the subject wherein the sequence includes a depth map including a 3D shape descriptor; and
   an interest shape estimation processor configured for:
      receiving the representations and segregating selected areas of the representations and converting the representations into subject shape descriptor values for comparison with the reference shape descriptor values;
      comparing the representations shape descriptor values with the reference shape descriptor values for identifying respiratory mechanics including identifying differences in the respiratory mechanics between the areas over a selected corresponding time varied sequence;
   generating a visual indicator of the difference for recommending actions to the subject for minimizing the differences; and
   displaying the visual indicator as difference maps representing the identified differences in depth and curvature domains of the 3D shape descriptor.

2. The system of claim 1 wherein the representations comprise a target region of interest of the subject.

3. The system of claim 2 wherein the target region comprises one of: the subject's anterior thoracic region, a region of the subject's dorsal body, and a side view containing the subject's thoracic region.

4. The system of claim 1 wherein the representations include a time-varying sequence of depth maps of a target region of interest of the subject being monitored for identification of the respiratory mechanics.

5. The system of claim 4 wherein the depth maps are selectively obtained from either images captured using an image-based depth sensing device comprising any of: a red green blue depth (RGBD) camera, an infrared depth camera, a passive stereo camera, an array of cameras, an active stereo camera, and a 2D monocular video camera, or from data captured using a non-image-based depth sensing device comprising any of: a LADAR device, a LiDAR device, a photo wave device, and a time-of-flight measurement device.

6. The system of claim 1 wherein the comparing comprises identifying differences in the selected areas includes differences in respiratory mechanics between two comparable portions of the target region of interest.

7. The system of claim 6 wherein the comparable portions comprise first and second lung areas of the subject and the identifying differences include determining different lung area expansion and contraction, respectively.

8. The system of claim 1 wherein the comparing includes recommending improved respiratory mechanics for achieving better subject health.

9. The system of claim 1 wherein the comparing includes obtaining a reference shape on the subject at a reference time and obtaining an estimated shape at a later time for tracking progress of respiratory health of the subject over time.

10. The system of claim 9 wherein the comparing includes obtaining a reference shape on the subject at a time that the subject is released from a hospital to track respiratory health of the subject over time since the hospital release.

* * * * *